United States Patent
Maguire et al.

(10) Patent No.: US 6,453,264 B1
(45) Date of Patent: Sep. 17, 2002

(54) SURFACE FLAW DETECTION USING SPATIAL RAMAN-BASED IMAGING

(75) Inventors: John Francis Maguire, Helotes, TX (US); John David Busbee, Wright-Patterson AFB; Steven R. LeClair, Spring Valley, both of OH (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/350,329

(22) Filed: Jul. 9, 1999

Related U.S. Application Data

(63) Continuation-in-part of application No. 08/846,437, filed on Apr. 30, 1997, now Pat. No. 6,038,525.

(51) Int. Cl.[7] .................................................. G01J 3/44
(52) U.S. Cl. .................... 702/172; 702/170; 356/301
(58) Field of Search .......................... 702/172, 22, 23, 702/27, 28, 30–32, 34, 35, 40, 66, 71, 75, 76, 81–84, 134, 170, 183, 189, 190, 193, 197, FOR 103, FOR 104, FOR 115–FOR 119, FOR 110, FOR 131, FOR 134, FOR 135, FOR 148, FOR 164, FOR 170; 427/8–10, 596, 166, 78, 96, 508, 593; 118/663–665, 670, 677, 679, 696, 697, 708, 712, 715; 204/192.13, 298.03; 356/301, 303, 237.1, 503, 504, 630; 117/85; 438/7, 8; 324/716, 229; 250/559.27, 559.26, 559.19, 2.22, 559.24; 382/144, 149, 145; 703/6, 7, 12

(56) References Cited

U.S. PATENT DOCUMENTS

| | | | |
|---|---|---|---|
| 4,024,291 A | 5/1977 | Willianns | 427/10 |
| 4,311,725 A | 1/1982 | Holland | 427/10 |
| 4,837,044 A | 6/1989 | Murarka et al. | 427/10 |
| 5,009,485 A | 4/1991 | Hall | 350/163 |
| 5,017,007 A | 5/1991 | Milne et al. | 356/301 |
| 5,112,642 A | 5/1992 | Wajid | 427/10 |
| 5,116,121 A | 5/1992 | Knoll et al. | 356/301 |
| 5,131,752 A | 7/1992 | Yu et al. | 356/369 |
| 5,208,648 A | 5/1993 | Batchelder et al. | 356/237 |
| 5,262,644 A | 11/1993 | Maguire | 250/339 |
| 5,354,575 A | 10/1994 | Dagenais et al. | 427/10 |
| 5,425,964 A | 6/1995 | Southwell et al. | 427/10 |
| 5,493,401 A | 2/1996 | Horie et al. | 356/382 |
| 5,518,759 A | 5/1996 | Sevillano et al. | 427/10 |
| 5,525,156 A | 6/1996 | Manada et al. | 118/118 |
| 5,535,128 A | 7/1996 | Laube et al. | 364/468.26 |
| 5,552,327 A | 9/1996 | Bachmann et al. | 437/8 |
| 5,592,282 A * | 1/1997 | Hartog | 356/301 |
| 5,665,214 A | 9/1997 | Iturralde | 204/298.03 |
| 5,786,893 A | 7/1998 | Fink et al. | 356/301 |

(List continued on next page.)

FOREIGN PATENT DOCUMENTS

| | | | |
|---|---|---|---|
| EP | 1 001 051 A1 | 5/2000 | C23C/16/52 |
| JP | 61994335 | 8/1986 | G01N/21/65 |
| JP | 0373580 | 3/1991 | H01L/39/00 |
| JP | 5102267 | 4/1993 | H01L/21/66 |
| JP | 59139929 | 11/1994 | B01J/19/08 |
| WO | 95/10768 | 4/1995 | G01N/21/88 |
| WO | 97/02465 | 1/1997 | G01B/11/00 |
| WO | 99/33101 | 7/1999 | H01L/21/66 |

Primary Examiner—Hal Wachsman
(74) Attorney, Agent, or Firm—Baker Botts L.L.P.

(57) ABSTRACT

A Raman-based spatial analysis method of detecting surface flaws. Special filters and optics are used to acquire filtered Raman response data from a portion of the surface. The filtered Raman response data represents the Raman response of the surface at a selected frequency. A camera records the response, thereby providing a two dimensional image of the portion of the surface. The image may be analyzed to determine whether that portion has desired thickness and chemical characteristics.

39 Claims, 7 Drawing Sheets

U.S. PATENT DOCUMENTS

| | | | |
|---|---|---|---|
| 5,835,221 A | 11/1998 | Lee et al. | 356/381 |
| 5,862,273 A * | 1/1999 | Pelletier | 356/301 |
| 6,038,525 A | 3/2000 | Maguire | 702/172 |
| 6,040,906 A * | 3/2000 | Harhay | 356/303 |

* cited by examiner

SURFACE FLAW DETECTION USING SPATIAL RAMAN-BASED IMAGING

RELATED APPLICATIONS

This application is a continuation-in-part application Ser. No. 08/846,437 of U.S. Pat. No. 6,038,525. filed Apr. 30, 1997, entitled, Process Control for Pulsed Laser Deposition Using Raman Spectroscopy.

The U.S. Government has a paid-up license in this invention and the right in limited circumstances to require the patent owner to license others on reasonable terms, as provided for by the terms of Contract No. TMC94-5801-0011-01 awarded by Wright Patterson Air Force Base.

TECHNICAL FIELD OF THE INVENTION

The present invention relates generally to control systems for manufacturing processes, and more particularly to a control system that uses Raman spectroscopy data to determine surface characteristics during formation of the surface.

BACKGROUND OF THE INVENTION

Pulsed laser deposition is a method of applying a film to the surface of a substrate material. Often the film is specified to be very thin. An example of an application of pulsed laser deposition is the deposition of superconducting films on various substrates. The desired thickness of these films is in the range of approximately 100 to 50,000 angstroms.

During the pulsed laser deposition process, the substrate is placed in a vacuum chamber together with a solid mass of target material. This target material is often a composition of materials, which will undergo a chemical reaction during the deposition process, thereby forming the desired deposit material. A high power laser has its beam incident on the target material. The laser vaporizes the target material, producing a plume. The plume diffuses toward the substrate and is deposited on the surface of the substrate.

A problem with pulsed laser deposition is that it is difficult to reliably and consistently achieve a desired morphology, physic-chemical structure, and thickness of the deposited film. Other important properties that vary because of inadequate process control are current-carrying capability, surface roughness, and response to radiation. The lack of process control is exacerbated as the size of the surface to be coated increases.

As an example of poor process control, in the case of a superconducting film of yttrium barium copper oxide, manufacturing inadequacies account for a wide variation in critical temperature. The best films have a critical temperature of 92 K, but in actuality, most films have a lower critical temperature.

A particular problem has arisen with the demand for long length superconducting wires. Superconducting materials tend to be inflexible, thus superconducting wires are often formed by depositing a thin layer of superconducting material on tape made from a more robust material. However, attempts to manufacture long lengths of such tapes have not been able to overcome the existence of defects. Any break in the conductive path will cause the entire wire to be defective.

SUMMARY OF THE INVENTION

One aspect of the invention is a computer-implemented Raman-based spatial imaging method of using a computer to detect flaws in a surface. The method is "spatial" in the sense that data for an array of points on the surface is acquired and processed, rather than data for just a single point. To accomplish real time processing speeds, the data for each point represents only selected Raman peak frequencies rather than an entire Raman spectrum.

More specifically, the method makes use of stored reference data representing at least one Raman peak of a reference surface. In operation, an area of the subject surface is illuminated. For each Raman peak of interest, Raman response illumination received from the illuminated area is filtered, with the filtering corresponding to the frequency of that Raman peak. The filtered illumination is recorded as a camera image, which represents an array of Raman response data. This image can be mapped to the area of the surface. Additional images can be obtained for additional Raman peaks. If the response data is then compared to the reference data, and appropriate analysis performed, the thickness or chemical composition of the surface can be determined.

DETAILED DESCRIPTION OF THE INVENTION

The following description begins in terms of pulsed laser deposition of thin films onto a substrate. Raman spectroscopy techniques may be used to monitor both the thickness and the chemical characteristics of the film. The "film" may be any dimension; it could be a film on a wafer, tape, or any other shape of substrate. The monitoring process could be applied during other types of deposition, not just laser deposition. Also, the same techniques could be used to measure thickness and determine chemical characteristics of existing films, anytime after deposition.

U.S. Pat. No. 6,038,525 describes these methods. The present application describes improvements to the methods, especially to a Raman-based spatial imaging improvement directed to detecting flaws in a surface. These improvements are especially useful during a film deposition process because they permit flaws to be corrected.

Overview of Pulsed Laser Deposition

Figure 1:
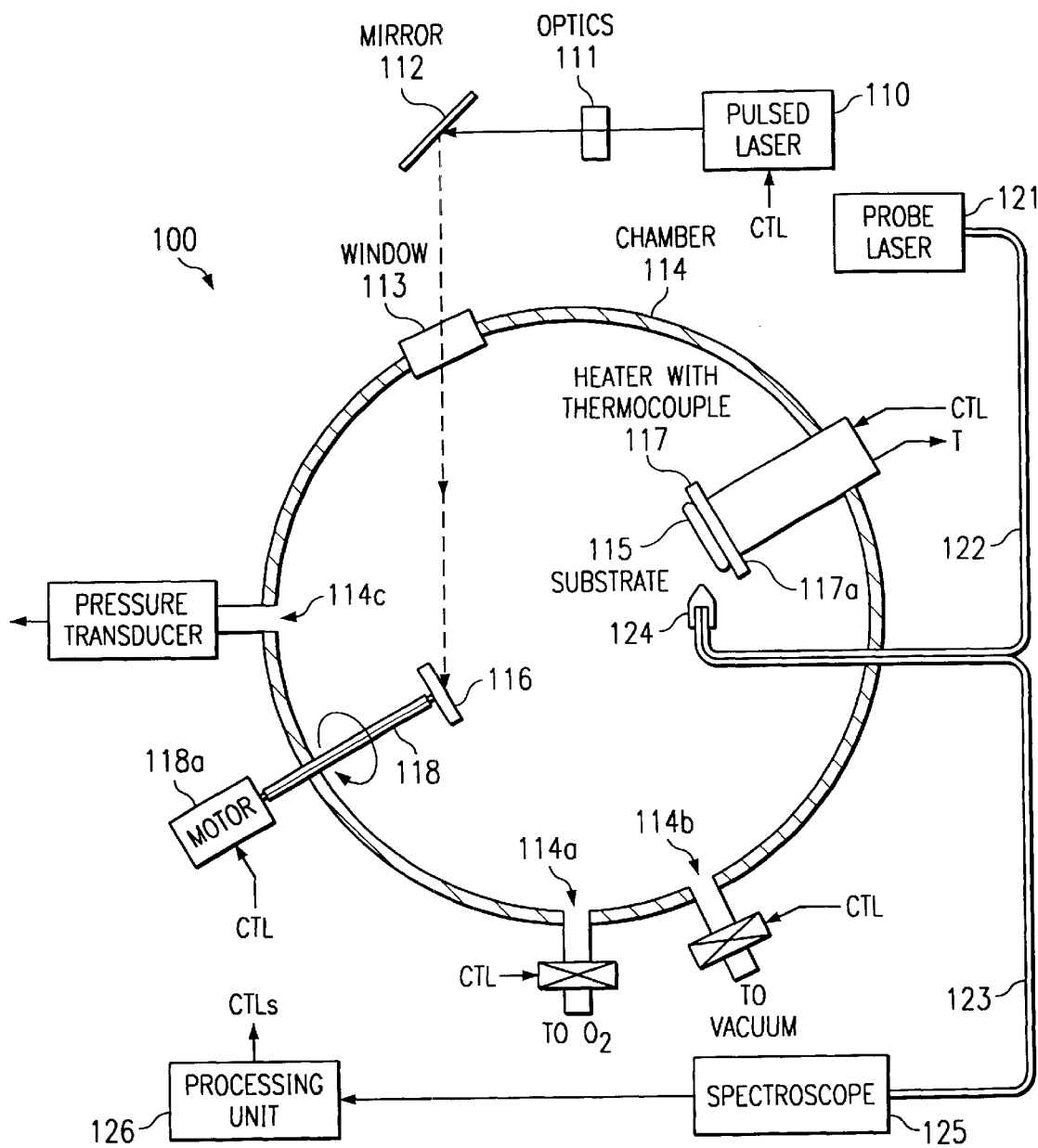
FIG. 1 illustrates a pulsed laser deposition system having a process control subsystem in accordance with the invention.

FIG. 1 illustrates a pulsed laser deposition (PLD) system 100, which is in data communication with a process control subsystem in accordance with the invention. As explained below, the process control subsystem is based on the spectroscopic response of the deposited material, specifically, Raman intensity and frequency shift data indicative of the current thickness and composition of the deposited material. The process control subsystem thereby provides a method for in-situ on-line measurements of film thickness as well as its chemical characteristics.

The process control subsystem is processor-based with a processor programmed to provide control decisions as well as thickness and composition data. The Raman response data is compared to data provided by models that represent desired characteristics of the deposited material. The comparison is used to make decisions about whether the deposition process is proceeding as desired and whether various PLD equipment controls should be adjusted. In sum, the process control subsystem of the invention implements closed loop, adaptive, intelligent process control.

PLD system 100, without the features of the present invention, is a conventional PLD system, such as those described in the Background. In operation, a pulsed laser 110 emits a beam of radiation of a desired wavelength. The laser beam passes through optics 111 that condition the beam. A mirror 112 directs the beam through a window 113 of a vacuum chamber 114.

Inside chamber 114 are a substrate 115 and a target 116. The substrate material 115 may be any material suitable for coating by PLD. Typically, substrate 115 is heated by means of a heating device 117 during the deposition process. A thermocouple 117a measures the temperature of the substrate 115, and provides a signal representing the current temperature, T. A control input (CTL) may be used to adjust the temperature.

The laser beam is directed to the target 116, which is mass of material that is typically disk shaped. The target 116 is placed on a rotating spindle 118, driven by a motor 118a. As the target 116 rotates, the beam hits different points on its surface. The target 116 is ablated by the beam, forming a plume that contains atomistic clusters of material to be deposited. Mirror 112 can be used to steer the laser beam to different radial points on the surface of target 116 so that consumption of the target material is maximized.

The vacuum chamber 114 has an oxygen valve 114a, which delivers oxygen to chamber 114. A pressure valve 114b maintains the desired pressure in chamber 114, typically a vacuum. A pressure transducer 114c measures the current pressure and provides a signal representing the current pressure, P. A control input (CTL) may be used to adjust the pressure.

Raman Spectroscopy for Monitoring Thickness and Chemical Characteristics

Although this description is in terms of monitoring a PLD process, the same concepts could be applied to any similar deposition process. For example, the target material could be ablated by means of an electron beam rather than a laser.

The process control subsystem comprises a probe laser 121, input optical fiber 122, output optical fiber 123, optical fiber end cover 124, spectroscope 125, and processing unit 126. During the PLD process, light from probe laser 121 is transmitted into the interior of chamber 114 via an input fiber optic probe 122. The light from the probe laser 121 is focused to a point on the surface of substrate 115 through the plume created by ablation of the target 116. The focusing provides a stronger output Raman signal as compared to that available with a diffused incident light. The end cover 124 may be designed with appropriate micro-optics to provide the desired focusing.

Light scattered from the substrate 115 is detected by a receiving optical fiber 123. This scattered light is transmitted to a spectroscope 125. Spectroscope 125 acquires a Raman signal that represents light scattered from the substrate 115 and the material currently deposited on substrate 115. The range of data provided by spectroscope 125 covers the Raman vibrational spectrum of both substrate 115 and the deposited material. As explained below, the Raman signal is characterized by frequency shifts and peak intensities that indicate the thickness and composition of the deposited material.

In addition to providing any desired optical effect, end cover 124 is designed to protect the end surfaces of the optical fibers 122 and 123. End cover 124 is resistant to deposition and ideally, is disposable.

Further details about the use of optical fibers to perform remote Raman spectroscopy, but without the process control features of the present invention, are set out in U.S. Pat. No. 5,262,644, to John F. Maguire, entitled "Remote Spectroscopy for Raman and Brillouin Scattering". A near-infra red laser is used to irradiate a sample of material to be analyzed. Optical fibers are used to carry the incident radiation to the sample, as well as to transmit scattered radiation back to appropriate equipment for performing Raman and Brillouin analysis. The described method avoids fluorescence while at the same time providing a signal having a strength and quality that are sufficient so as to permit accurate analysis. This patent is assigned to Southwest Research Institute and incorporated by reference herein.

Figure 2:
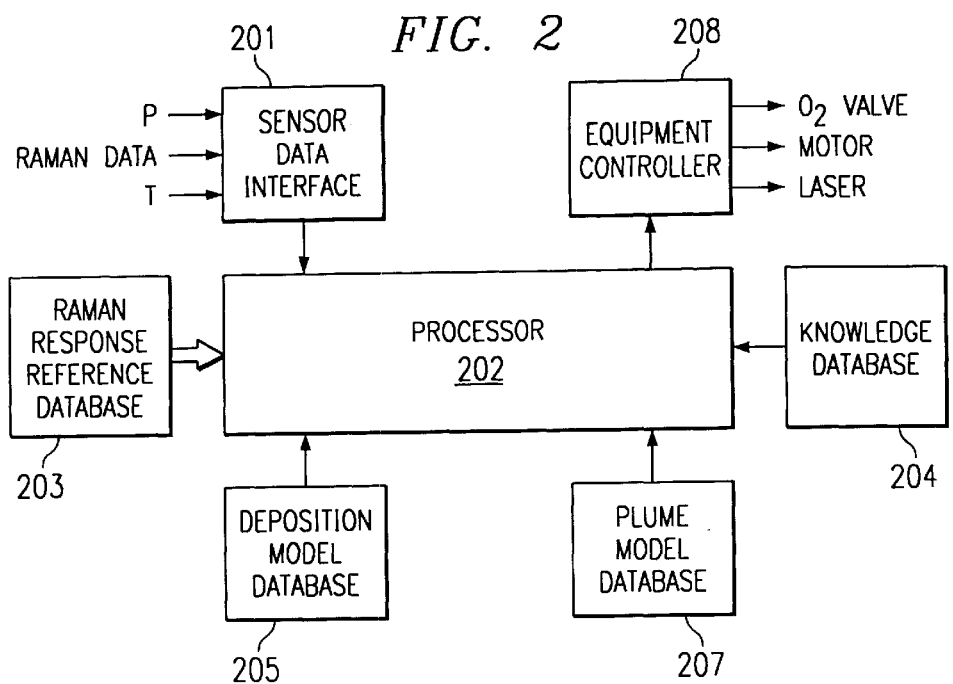
FIG. 2 is a block diagram of the processing unit of FIG. 1.

FIG. 2 is a block diagram of the processing unit 126 of FIG. 1. It receives the Raman signal acquired by spectroscope 125. As explained below, processing unit 126 is a processor-based expert system, capable of providing a wide range of control decisions.

A sensor data interface 201 accepts the Raman signal as digital values. It may also receive and digitize signals representing temperature, T, and pressure, P.

A processor 202 accesses the data from sensor data interface 201 as well as data from a reference database 203 and from model databases 205 and 207. As explained below, the reference database 203 stores Raman response data from the bare substrate 115 as well as Raman response data from a "ideal" film. The model databases store model data, which represents kinetic aspects of the PLD process and provides a basis for decision-making functions of processor 202.

Figure 3:
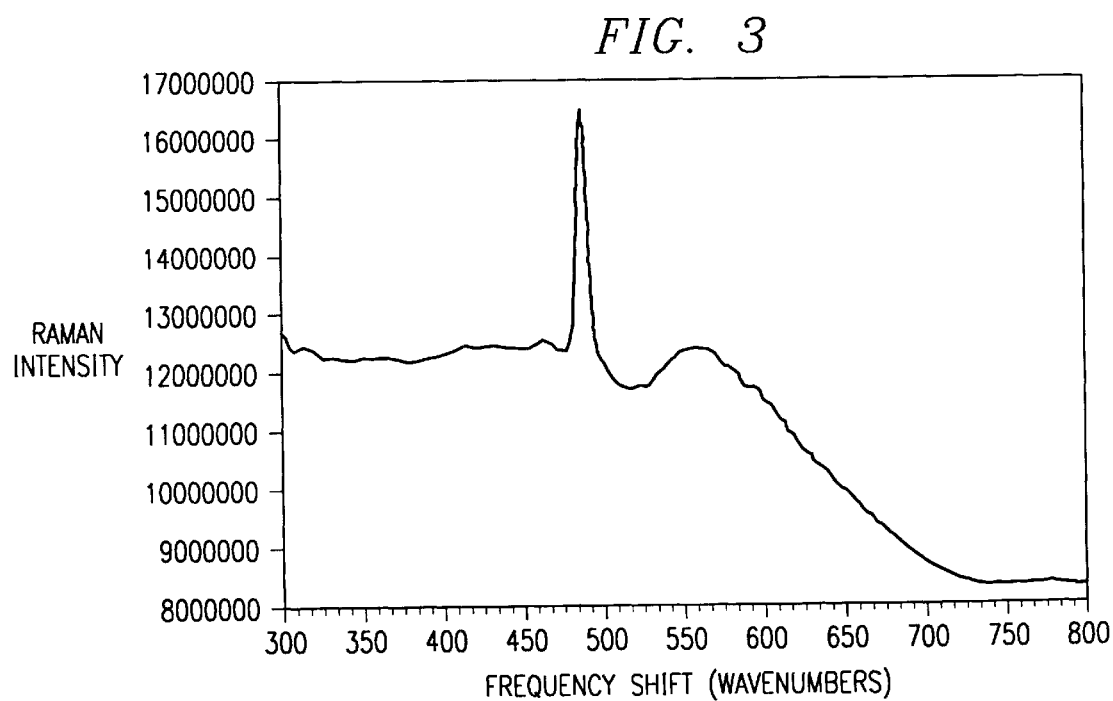
FIG. 3 illustrates substrate reference data, specifically, the Raman peak of a bare substrate, to be used in measuring thickness of a deposited film.

FIG. 3 illustrates one type of reference data that may be stored in reference database 203. The reference data of FIG. 3 is referred to herein as "substrate reference data" and represents the Raman spectrum of a substrate 115 that is uncoated or has a known film thickness. In the example of this description, the substrate 115 is bare $LaALO_3$ (lanthanum aluminum oxide) with a strong Raman peak at 485 $cm^{-1}$.

Figure 4:
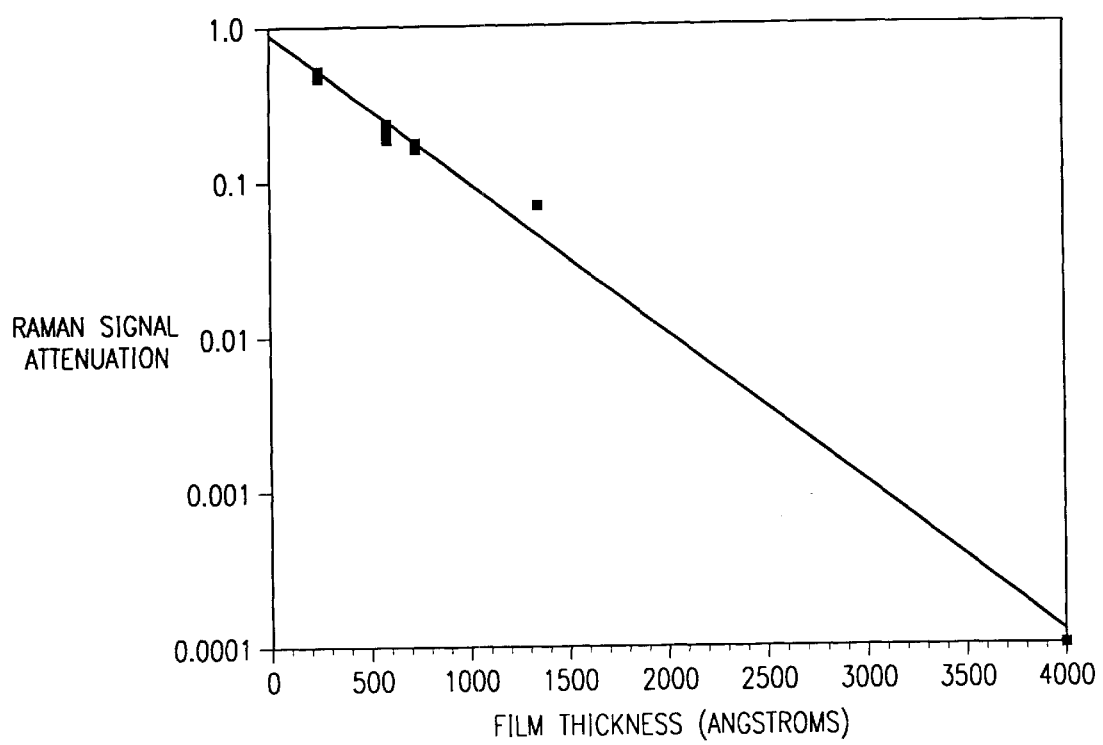
FIG. 4 illustrates the relationship between film thickness and attenuation of the Raman peak of FIG. 1.

FIG. 4 illustrates how processor 202 may be programmed to determine film thickness during the deposition process. In the example of FIG. 4, the deposited film is YBCO (yttrium barium copper oxide). During deposition, the Raman peak associated with the substrate 115 attenuates as a function of increasing film thickness. The signal attenuation is expressed logarithmically, and the attenuation is exponential. For a given signal attenuation, the film thickness is known. Even for film thicknesses in the range of 0–1000 angstroms, the attenuation is a full power of 10, making the thickness measurement sensitive to even these very thin depositions. Thus, processor 202 may be programmed to compare data acquired from spectroscope 125 to reference data to determine the current thickness of the film.

Figure 5:
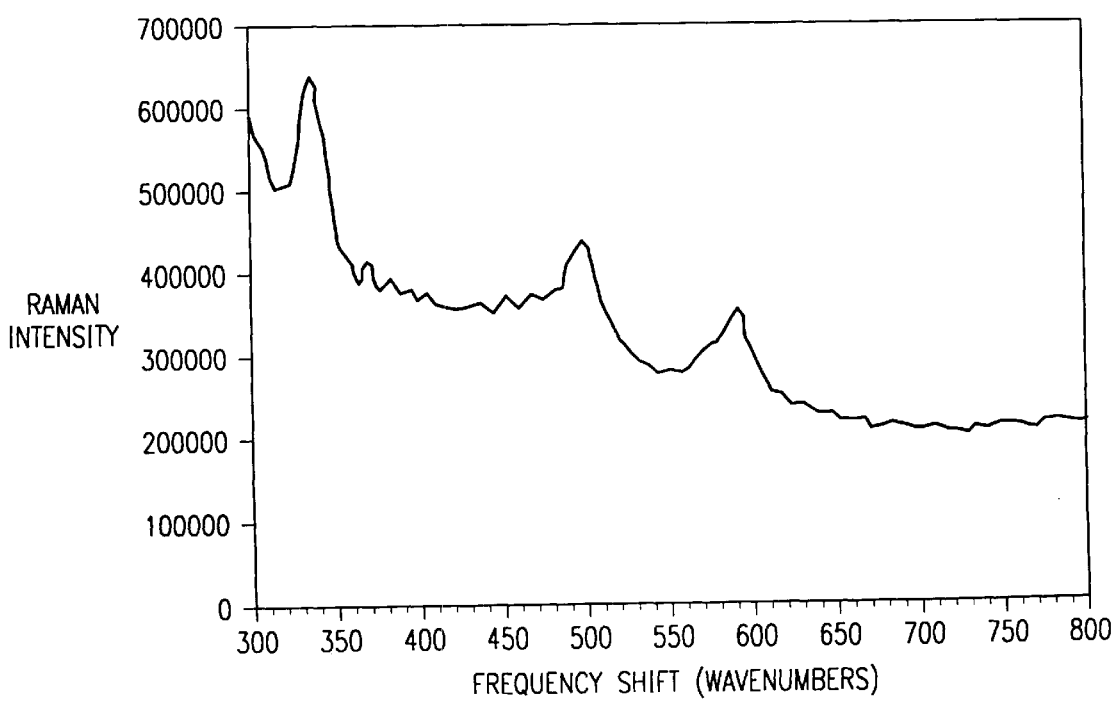
FIG. 5 illustrates film reference data, specifically, the Raman peaks of an ideal film, to be used in determining chemical characteristics of a deposited film.
Figure 6:
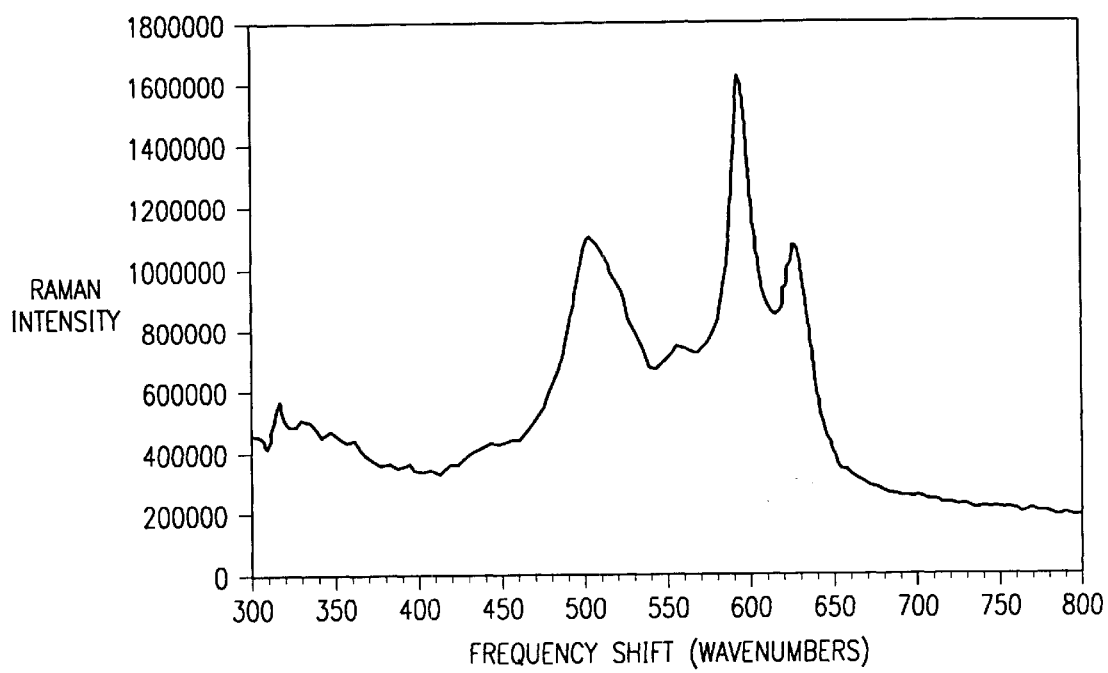
FIG. 6 illustrates film response data.
Figure 7:
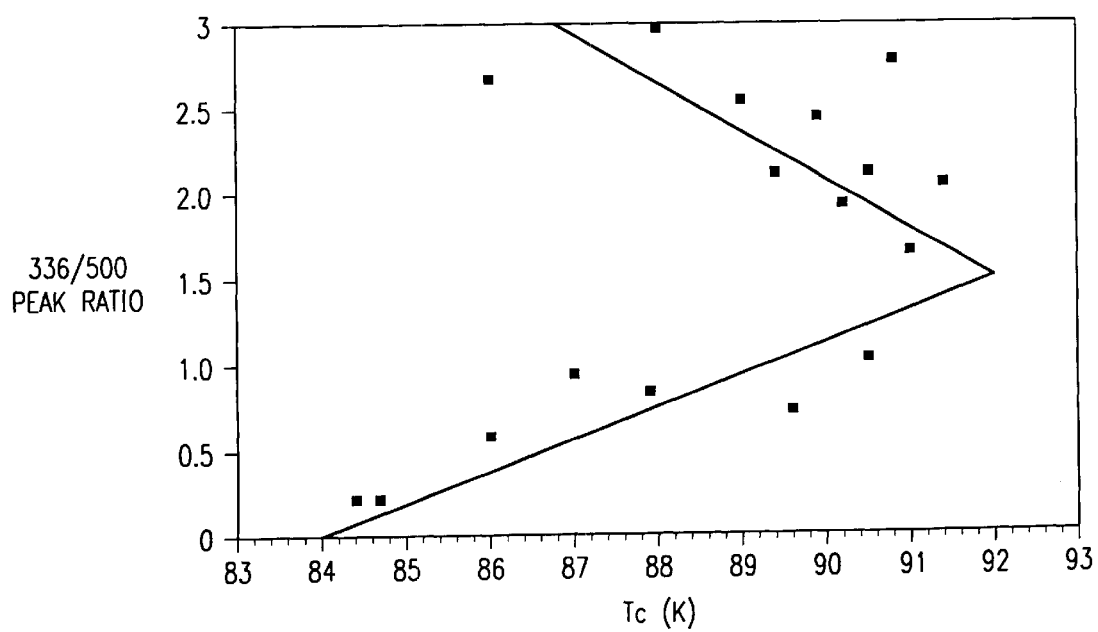
FIG. 7 illustrates Raman peak ratios versus critical temperature values for a particular film.
Figure 8:
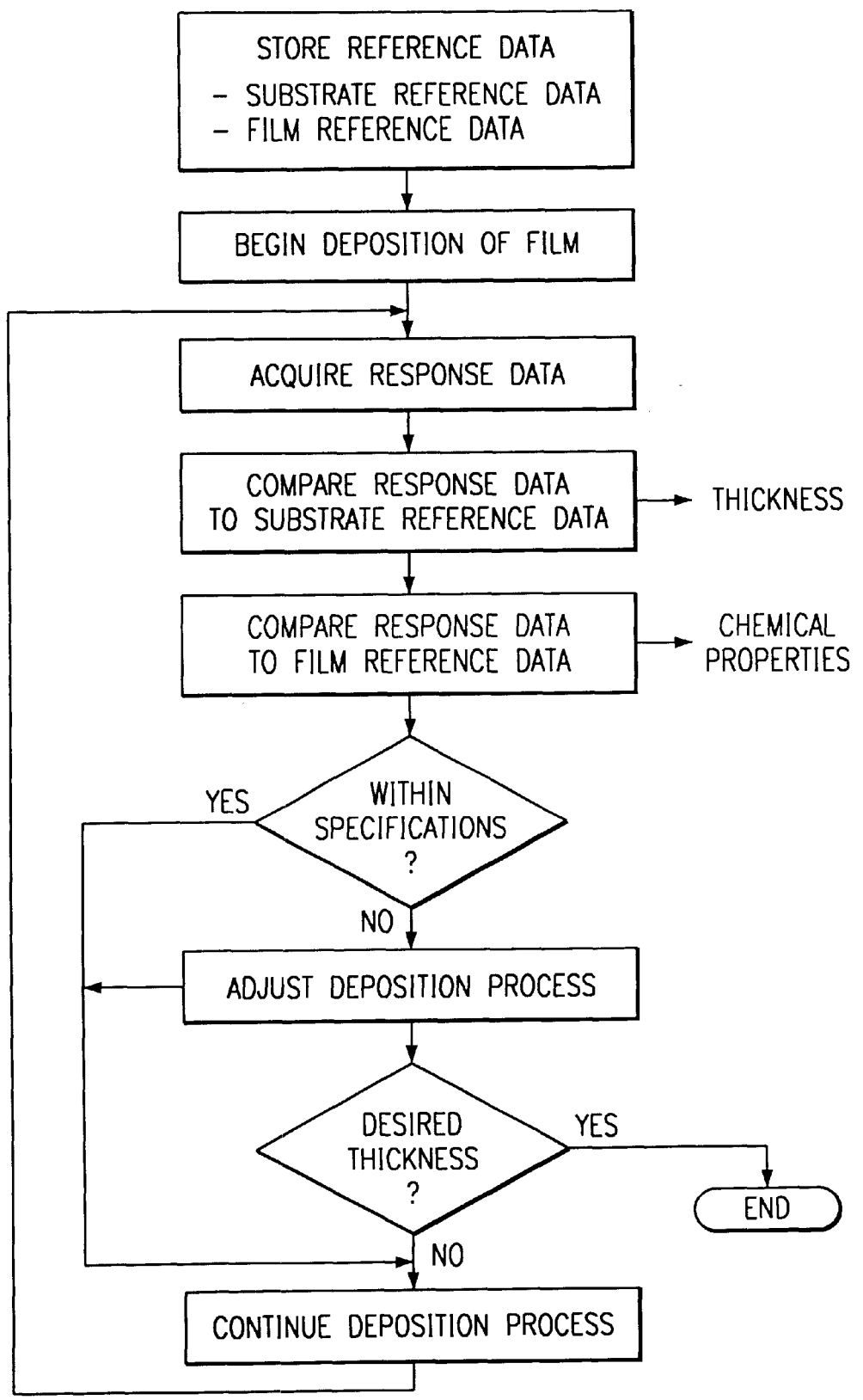
FIG. 8 illustrates the process of using Raman analysis to measure thickness and chemical composition.

FIGS. 5–7 illustrate how processor 202 may be programmed to determine the chemical composition of the film as it is being deposited. Again, the substrate 115 is $LaAlO_3$. Target 116 is a composite material that is intended to produce YBCO. As material is deposited to provide a film of increasing thickness, the spectrum of the substrate 115 is obscured and the Raman spectrum of the film develops. In the example of FIGS. 5–7, the Raman spectrum is used to indicate the film's critical temperature, $T_c$, which is a function of chemical properties of the film.

FIG. 5 illustrates the Raman signal from an "ideal" film having a desired critical temperature, whereas FIG. 6 illustrates a deposited film having an unacceptable critical temperature. The peaks at 336 $cm^{-1}$, 486 $cm^{-1}$, and 500 $cm^{-1}$ are due to the desired phase of YBCO, whereas the peaks at 600 $cm^{-1}$ and 640 $cm^{-1}$ are tentatively assigned to a 211 phase ($Y_2BaCuO_5$) and barium cuprate ($BaCuO_2$). These are non-superconducting phases or materials that can form during the PLD process. It has been experimentally determined that superconducting films with no peak at 600 $cm^{-1}$ do not perform as well as superconducting films with a modest peak at 600 $cm^{-1}$. It also appears that a process that produces a small quantity of the 211 phase provides better superconducting films.

FIG. 7 illustrates the Raman peak ratios versus the critical temperature values for the $LaAlO_3$ substrate 115 and YBCO deposition. The 336/500 peak ratio is correlated with the critical temperature. A ratio of 1:5 indicates the highest critical temperature, $T_c$.

As indicated by FIGS. 5–7, processor 202 may be programmed to compare reference data representing films having known characteristics to response data representing the film as it is being deposited. These comparisons can be used to determine the chemical composition of the film and to thereby indicate properties of the film.

In general, a characteristic of a Raman signal scattered by a particular material is that the Raman peaks are proportional to the concentration of that material. If the concentration is related to a particular property (such as critical temperature) reference data can be obtained and stored to represent what concentration is desired to obtain that property in the deposited film. The Raman response from the deposited film can be compared to the reference data to determine whether that concentration is present.

As stated above, processor 202 may also access model data. In the example of this description, there are two main types of models for any given substrate/film combination—a deposition model and a plume model, which are stored in databases 205 and 207, respectively.

The deposition model database 205 stores a model that represents a reference rate of increase in thickness of the deposited film. A plume models database 207 represents reference rates of change of the "plume", which is the region in which the material is diffused within chamber 114. The plume models represent both the transport and the reaction characteristics of the ablated target material. These models are based on the recognition that the target 116 responds to the laser ablation in two ways—it undergoes a chemical reaction as well as a physical diffusion. The reaction model includes kinetic representations of the chemical transformations. The transport model includes representations of diffusion rates.

The model data permits processor 202 to be programmed to determine whether rates of change of the deposited film satisfy modeled rates of change. Typically, the model data represents conditions that are desired, but could also represent conditions to be avoided. In either case, for purposes of this description, the model data is referred to herein as "reference" model data.

The models may be expressed in terms of changes in concentration as a function of time, that is, a rate of change in concentration. This permits the model data to be directly compared to data from spectroscope 125.

Using the model data, processor 202 may be programmed to make decisions based on both the Raman response data and the model data. For example, the Raman response might indicate that a certain desired chemical structure is not present in the deposited film. The processor 202 may then determine whether the model data indicates that a reaction is occurring too slowly or that the material is not being transported properly. Similarly, the Raman response data might indicate that the film is becoming thick too quickly as compared to the model data. These are but two examples of the many conditions that can be indicated with the model data.

If processor 202 determines that the PLD process is not occurring in a satisfactory manner, it is further programmed to take some action. It may simply display a message indicated the state of the process, or it may activate one or more automated equipment controls. In the latter case, the processor 202 determines which equipment control parameter can be adjusted to vary the rate of reaction or diffusion. Referring again to both FIGS. 1 and 2, the various equipment control parameters typically include the energy emitted by laser 110, the spinning rate of motor 118, the amount of oxygen released by valve 114a. A controller 208 provides appropriate control signals to these various equipment controls.

As a specific example of decision-making by processor 202, referring again to FIGS. 4 and 5, the peaks in the Raman spectrum are vibrational frequencies associated with metal-oxygen bonds. Raman intensities are related to the amount of oxygen in the deposited film, which can be controlled via oxygen input valve 114a.

Knowledge base 204 may include heuristic rules for making determinations about whether the PLD process is occurring satisfactorily. For example, comparison of response and model data might indicate that the deposit is thinner than expected at a given time, but that its structure and rate of growth are satisfactory. These conditions might warrant a different action than would conditions where the deposit is not thick enough accompanied by an unacceptable rate of growth or structure.

As stated above, equipment data such as pressure and temperature are also available as inputs to processing unit 126. Processor 202 could be further programmed to compare current pressure and temperature values to desired conditions, to use them in the heuristic determinations, and to take some action. The actions may include adjustment of equipment control or simply checking equipment conditions such as pressure or temperature so that further analysis can be made.

Raman Analysis of Metallic Materials

All materials provide a Raman response. With appropriate filtering, the above methods of analysis can be applied to metallic surfaces. Such surfaces tend to be highly reflective and present problems in signal detection, resulting from intense Rayleigh lines. However, rejection filters can be designed to filter these Rayleigh lines and permit the above methods to be applied to metal surfaces. An example of a suitable filter is a Bragg filter.

Spatial Raman Imaging for Flaw Detection

As explained in this section, as an alternative to acquiring a Raman spectrum from points on the substrate, special optics and a camera can be used to acquire a two-dimensional image from an area of points on the substrate. The optics are used to filter the Raman response illumination, such that the filtered Raman response is of only a selected frequency that corresponds to a desired Raman peak. The two-dimensional image can then be mapped to the area of points on the substrate. Each pixel element of the image indicates whether a corresponding point on the substrate has the desired Raman peak. Images for additional Raman peaks can be collected in a similar manner, and multiple images can be combined and analyzed.

The following description is mostly in terms of generating Raman response data that is two-dimensional. However, for generality, the same concepts apply to one-dimensional arrays of data. As explained below, the common characteristic is that the data is "spatial", representing more than one point on the substrate. Each point is represented by extracted Raman peak data, rather than by a Raman spectrum.

The following description is in terms of depositing films on "long wire" substrates, long wires being particularly difficult to manufacture without flaws. However, it can be easily understood that the same concepts apply to monitoring deposition of films on substrates of any shapes. For example, as semiconductor wafers increase in size, there is a need for improved methods of ensuring manufacturing quality.

It should also be understood that the flaw detection methods described herein could be applied to any surface, coated or uncoated. It could be applied to existing materials, not just during manufacture. An additional example is flaw detection in an optical coating on a large mirror to be placed in outer space, where the mirror is the "substrate". In general, the methods can be applied to detecting flaws in any surface material, whether coated or uncoated, that is amenable to Raman analysis.

Figure 9:
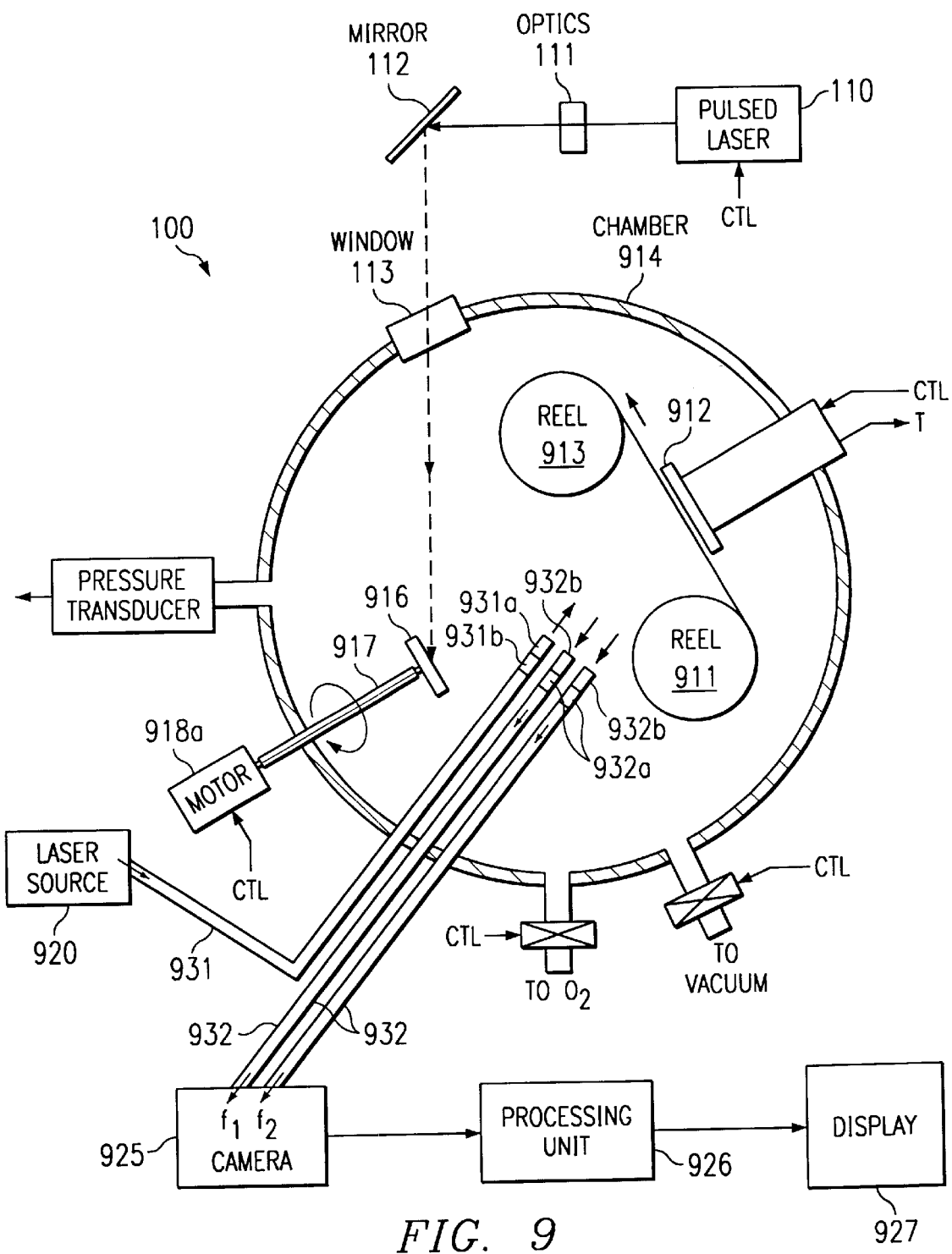
FIG. 9 illustrates a deposition system for providing Raman-based spatial imaging in accordance with the invention.

FIG. 9 illustrates a pulsed laser deposition system 900, with two-dimensional Raman imaging in accordance with the invention. As in the system of FIG. 1, the deposition occurs inside a deposition chamber 914. Laser light is directed through a window 913 toward target material 916, which is ablated to form a plume of material that accumulates on the substrate.

The substrate is any long thin material transportable across the platform 912 from a first reel 911 to a second 913. Thus, a "source" wire is the substrate upon which a film is to be deposited. In FIG. 9, the source wire is stored on reel 911, which is unwound past the deposition platform 912 where the deposition occurs. The coated wire is then wound onto a take-up reel 913. As in the system of FIG. 1, platform 912 may have means for heating the substrate.

A light delivery tube 931 extends into the chamber 914. Tube 931 delivers high intensity laser light, via optical fibers, toward the platform 912. The lens 931a at the output end of tube 931 defocuses the light onto a portion of the substrate that is on platform 912. A filter 931b filters out interference, such as interference from the fiber optic media. Lens 931a and filter 932b may be implemented with a microlens and a deposited filter, respectively, at the end of the optical fibers.

Light collection tubes 932 receive Raman scattered light from the illuminated surface, via optical fibers. Each light collection tube has a receiving lens 932a. As explained below, the filter 932b for each collection tube 932 is different, such that each tube 932 receives only a selected "Raman peak" frequency of Raman-scattered light. In the example of FIG. 9, there are two Raman peak frequencies of interest: f1 and f2.

Figure 10:
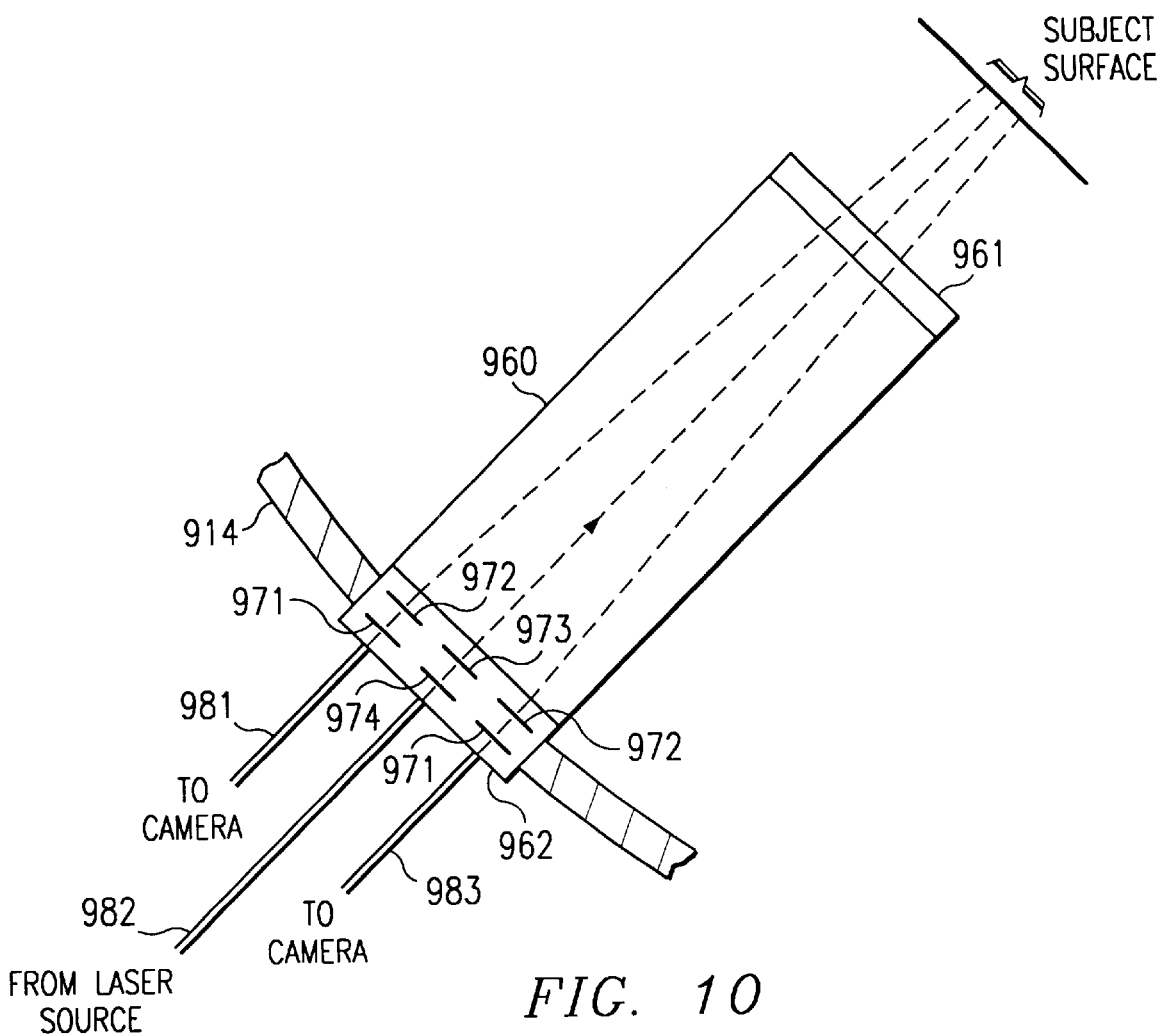
FIG. 10 illustrates a light pipe alternative to the fiber optic tubes of FIG. 9.

FIG. 10 illustrates a light pipe 960, which is an alternative to the fiber optic light transmitting tube 931 and light collection tubes 932. Light pipe 960 is hollow; within its interior, light is transmitted to, and received from, the subject surface. As in the example of FIG. 9, there are two Raman peak frequencies of interest, and thus two paths of Raman response illumination travel are collected by light pipe 960. A replaceable window 961 permits light to exit and enter light pipe 960. A flange connector 962 connects the light pipe 960 to the wall of chamber 914. Within connector 962, are the lens 973 and filter 974 for the transmitted (Raman excitation) illumination, as well as the lenses 972 and filters 971 for the received illumination. Because the lenses and filters are within flange connector 962 and not on the ends of fibers, conventional optical devices may be used. Fibers optics 982 may be used to carry the illumination from laser source 920 to the light pipe 960. Fiber optics 981 and 983 may be used to carry the illumination from light pipe 960 to the camera 925.

In the example of FIG. 9, the light tube 931 illuminates platform 912, and light tubes 932 receive the Raman scattered light from the substrate as the film is being deposited. However, the tubes 931 and 932 could also be "aimed" at the substrate at any point after deposition of the film.

The light received from light collection tubes 932 is delivered to a camera 925, which records a two-dimensional image from each of the tubes 932. Regardless of the aim of tubes 932, each provides camera 925 with successive images of data as the substrate passes within its field of view.

An example of a suitable camera 925 is a CCD array, which records a digital array of pixel element values. However, regardless of the type of camera 925, the result is an image, analog or digital, which represents the filtered Raman response of the subject surface. Analog images can be quantitized with appropriate processing. Each pixel element has an associated intensity.

The images are delivered to processing unit 926, which has appropriate processing and memory for analyzing the images. As explained below, flaw detection involves some sort of comparison of the response data to reference data, to determine whether the condition (thickness or chemical composition) of the subject surface meets one or more quality metric.

With respect to the reference data, processing unit 926 stores data derived from selected Raman peaks of a reference material. Typically, the reference material is an "ideal" reference material, whose chemical characteristics are those desired for the material being manufactured. In the case of film deposition, the reference material would be a substrate having the desired film. The Raman image of the reference material has been previously analyzed to determine the Raman peaks of interest. A typical reference material might have only two or three peaks of interest. For each peak, a certain center frequency and bandwidth is selected.

For example, referring again to FIG. 5, the desired material might have Raman peaks at wavenumbers of 336 and 500 $cm^{-1}$. Each Raman peak has an expected position and height. In effect, this peak information is extracted from the complete Raman spectrum of the reference material.

In a simple embodiment, the reference data could represent a single ideal point. Or, Raman peak data from an array of points could be collected. In the latter case, the reference data may be in the form of a two-dimensional reference image. Where the reference material has more than one Raman peak of interest, reference data can be stored for each peak or the peak data could be combined. In the latter case, the result would be point data or array data, each point value representing represent the combined peak frequencies and intensities at that point. Image processing techniques can be used to associated different frequencies with different colors so that a combined image has the combined colors and intensities at each pixel element.

The reference data determines the filtering provided by optics 932. In other words, as stated above, light tubes 932 are filtered to receive light at the Raman peak frequencies of the reference material. Each peak frequency has a selected bandpass.

Referring again to the example of FIG. 9, camera 925 receives two images, one from each light collection tube 932. Each image corresponds to one of the Raman peak frequencies, f1 and f2. The number of light collection tubes 932 (the number of Raman peak frequencies for which images are recorded) may vary depending on the Raman spectrum of the reference material. However, as stated above, a typical material can be characterized by only two or three Raman peaks.

The images recorded by camera 925 are delivered to processing unit 926. For each image, the intensity of the response illumination at a given pixel element represents the Raman intensity.

Each image may be associated with a different color. Continuing the example of FIG. 5, a first image represents the 336 $cm^{-1}$ peak, and might be associated with the color red. A second image represents the 500 $cm^{-1}$ peak, and might be associated with the color blue.

Figure 11:
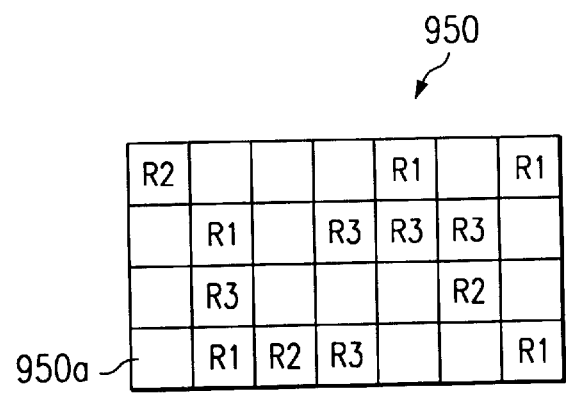
FIG. 11 is a simplified example of an image obtained from one of the light collection tubes of FIG. 9.

FIG. 11 illustrates a two-dimensional array 950 of Raman response data such as might be provided by camera 925. The data has been color coded to form a color image. An advantage of color coding the data in the manner is that it provides easily interpreted output at display 927. The frequency of light collected by the tube 932 has been associated with the color red. There are three red intensities, ranging from R1 to R3. The array 950 is mapped to the portion of the substrate from which the response data has been collected. Thus, each pixel element 950a represents a point on the substrate. As indicated by the response data, the film being deposited has Raman peaks at some points, some points having greater Raman intensity than others.

Processing unit 926 analyzes the Raman response images, using some sort of comparison to the reference data. Several examples are described below. Regardless of the type of analysis, each point of response data is analyzed in terms of a selected frequency, rather than in terms of a complete Raman response. This permits the analysis to be performed in real time.

Typically, the reference data as well as the response data will be in the form of an array of points. However, in theory, a single reference point could be used as an "ideal" metric of interest. Where both the reference data and the response data are image arrays, various pattern recognition techniques may be used.

As one example of analysis, continuing the two-peak example, where two arrays of response data have been acquired, processing unit 926 could combine the data to generate a third array of response data. This third array could be color coded to form an image with reds, blues, and combinations of these colors. The result is an array of pixel elements, each of which represents the extent to which the desired film has been deposited on the material at a point mapped to the pixel element. The response data can be compared to the reference data that has been similarly obtained and processed (or to a single reference point value) to determine if the surface is flawed.

The analysis might involve variations of the reference data as well as the response data. For example, for films, the feature of interest might be thickness rather than chemical composition. In a manner analogous to the non-spatial thickness analysis described above in connection with FIG. 4, the Raman response of the substrate could be referenced. In accordance with spatial imaging, the reference data is a two-dimensional array of Raman peak values. Then, an image representing the Raman peaks of the coated substrate could be captured and compared to the reference image. The thickness of the film is indicated by attenuation of the substrate response. For example, for display, a red image representing the uncoated substrate might turn to green, indicating that the substrate is being coated with a film represented by a green image.

The ratio of the peaks of the Raman response images can also be the subject of analysis. For example, as explained above in connection with FIG. 7, the ratio of two peaks can indicate the superconductive properties of the deposited film. This ratio data can be obtained by quantifying the intensities of the image associated with each peak. After appropriate calculations, the resulting two-dimensional data can be color-coded into a third image that represents the current-carrying capability of the film. In the example of FIG. 7, a high ratio is desired, but for other applications, low ratios, uniform ratios, or inverted ratios might be the measure of quality.

A feature of the invention is that once flaws are detected, the flaw can be corrected. For example, if a flaw is detected in the system of FIG. 9, reel 911 can be re-wound so that the flawed portion of the substrate is once again in the platform 912. The substrate can be re-coated with additional film material. If desired, the defective film can be removed prior to the re-deposition.

In the case of film deposition to make conducting wires, the image can be analyzed to determine if there is a conducting path through the length of the wire. In other words, the complete surface need not be conductive so long as a sufficient path has been formed. If there is no path, the wire can be re-wound and the film re-deposited. A specific example of analysis of long wires, is one that determines whether there are regions of "percolation" on the film, which can prevent desired electron activity.

In general, when the flaw detection method is applied during a materials manufacturing process, the flaw can be corrected by adjusting the process. The "adjustment" may be re-deposition of a film, or some other process control, such as adjusting chemical inputs, temperature, or other process parameter.

The color coding of the response images can be arbitrary or can follow a scheme. Raman peaks can be color coded in an order corresponding to the natural order of color frequencies in white light. However, for some materials and types of analysis, an inverted or jumbled ordering might better highlight the feature that is the subject of analysis.

The two dimensional imaging discussed above can be extended to three dimensional imaging. If the surface being analyzed has some degree of transparency, light collection tubes 932 can be focused to receive response data from different depths. In the case of film deposition, the Raman response of the film at various stages of deposition can be recorded for a third (depth) dimension of data.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A Raman-based spatial imaging method of using a computer to detect flaws in a surface, comprising the steps of:

storing reference data representing at least one Raman peak of a reference surface;

illuminating an area of a subject surface;

filtering Raman response illumination received from the illuminated area, the filtering corresponding to the frequency of the at least one Raman peak of the reference surface;

recording an array of response data representing the filtered Raman response;

mapping the array of response data to the area of the subject surface; and comparing the reference data to the array of response data to determine the thickness of the subject surface.

2. The method of claim 1, wherein the reference data is an array of reference data, and wherein the comparing step is performed by comparing the array of response data to the array of reference data.

3. The method of claim 1, wherein the reference data represents more than one Raman peak, and wherein the filtering and recording steps are repeated for one or more additional Raman peaks.

4. The method of claim 3, wherein the reference data comprises one or more Raman peak ratio values, and the comparing step generates Raman peak ratio values for the array of response data.

5. The method of claim 1, wherein the recording step is performed by a camera that acquires a one dimensional array.

6. The method of claim 1, wherein the recording step is performed by a camera that acquires a two dimensional array.

7. The method of claim 1, wherein said comparing step is performed by analyzing chemical properties of the subject surface by determining the extent to which the reference data and the array of response data are similar.

8. The method of claim 1, wherein the subject surface is a film coating on a substrate, wherein the reference data represents the Raman peak data of a reference substrate, and wherein the comparing step is performed by analyzing the thickness of the film coating by determining attenuation of the reference data in the array of response data.

9. The method of claim 1, further comprising the steps of color coding the array of response data for display.

10. A Raman-based spatial imaging method of using a computer to detect flaws in a subject film on a substrate during a deposition process, comprising the steps of:

storing reference data representing at least one Raman peak of a reference film;

depositing at least a portion of the subject film on the substrate;

illuminating an area of the subject film;

filtering Raman response illumination received from the illuminated area, the filtering corresponding to the frequency of the at least one Raman peak of the reference film;

recording an array of response data representing the filtered Raman response;

mapping the array of response data to the subject film; and comparing the reference data to the array of response data to determine whether the chemical composition of the subject film is satisfactory; and adjusting the deposition process if the comparing step determines the subject film to be not satisfactory.

11. The method of claim 10, wherein the reference data is an array of reference data, and wherein the comparing step is performed by comparing the array of response data to the array of reference data.

12. The method of claim 10, wherein the reference data represents more than one Raman peak, and wherein the filtering and recording steps are repeated for one or more additional Raman peaks.

13. The method of claim 12, wherein the reference data comprises one or more Raman peak ratio values, and wherein the comparing step generates Raman peak ratio values for the reference data.

14. The method of claim 10, further comprising the steps of color coding the array of response data for display.

15. A Raman-based spatial imaging method of using a computer to detect thickness of a subject film on a subject substrate during a deposition process, comprising the steps of:

storing reference data representing at least one Raman peak of an uncoated reference substrate;

depositing at least a portion of the subject film on the subject substrate;

illuminating an area of the subject film;

filtering Raman response illumination received from the illuminated area, the filtering corresponding to the frequency of the at least one Raman peak;

recording an array of response data representing the filtered Raman response;

mapping the array of response data to the area of the subject film;

comparing the array of response data to the reference data to determine whether the thickness of the subject film is satisfactory; and depositing additional film on the subject substrate if the comparing step determines the thickness to be insufficient.

16. A processing system for performing Raman-based spatial analysis of a surface, comprising:

a reference database that stores reference data for at least one reference material, the reference data representing one or more Raman peaks of a reference surface; and a processor operable to perform the following processes: to receive response image data representing a filtered Raman response from an area of a subject surface, the filtering corresponding to a frequency of a Raman peak of the reference surface; to map the response image data to the area of the subject surface; and to compare the reference data to the response image data to determine the thickness of the subject surface.

17. The processing system of claim 16, wherein the reference data is an array of reference data, and wherein the processor compares the response image data to the array of reference data.

18. The processing system of claim 16, wherein the reference data represents more than one Raman peak, and wherein the processor receives an image for each of the one or more additional Raman peaks.

19. The processing system of claim 16, wherein the processor analyzes the chemical properties of the subject surface by determining the extent to which the reference data and the response image data are similar.

20. The processing system of claim 16, wherein the subject surface is a film coating on a substrate, wherein the reference data represents the Raman peak data of a reference substrate, and wherein the processor analyzes the thickness of the film coating by determining attenuation of the reference data in the response image data.

21. A method of using a computer to measure the thickness of a film coated upon a subject substrate, comprising the steps of:
   storing substrate reference data representing a waveform of the Raman response of a reference substrate;
   acquiring substrate response data representing the Raman response of a subject substrate having a film with unknown thickness;
   filtering out Rayleigh line effects in the substrate response data;
   comparing the frequency shift peak intensity of the substrate reference data and the substrate response data;
   determining the attenuation of the waveform represented by the substrate reference data; and
   estimating the thickness of the film, using the results of the comparing and determining steps.

22. The method of claim 21, wherein the method is performed during a deposition process during which the film is deposited upon the subject substrate.

23. The method of claim 22, further comprising the steps of storing deposition model data representing a reference rate of thickness change and of determining whether said deposition process is satisfactory on the basis of said deposition model data.

24. The method of claim 22, further comprising the step of determining an equipment control action to be taken if said estimating step is not satisfactory.

25. The method of claim 24, wherein said deposition process is a deposition process performed by a laser and wherein said equipment control action is with respect to said laser.

26. The method of claim 24, further comprising the step of receiving equipment data representing conditions of said deposition process and wherein said equipment control action is further based on said equipment data.

27. The method of claim 21, wherein the acquiring step is performed by irradiating said film via optical fiber and acquiring a Raman response.

28. The method of claim 21, wherein the acquiring step is performing by irradiating said film and acquiring the Raman response via optical fiber.

29. The method of claim 21, wherein said acquiring step is performed by irradiating said film with near infra red light and acquiring a Raman response.

30. A method of using a computer to monitor deposition of a subject film being deposited upon a substrate, comprising the steps of:
   storing film reference data representing the Raman response of a reference film having known chemical characteristics;
   acquiring film response data representing the Raman response of said subject film during said deposition;
   acquiring substrate response data representing the Raman response of the substrate;
   filtering the results of said acquiring step from the Raman response of said substrate;
   filtering out Rayleigh line effects in the film response data;
   comparing the peak characteristics of said film reference data and said film response data; and
   controlling the deposition on the basis of said comparing step.

31. The method of claim 30, further comprising the steps of storing model data representing a reference rate of change of said deposition and of determining whether said known chemical characteristics are changing at a satisfactory rate.

32. The method of claim 30, further comprising the step of determining an equipment control action to be taken if said known chemical characteristics are not satisfactory.

33. The method of claim 32, wherein said deposition is performed by a laser and wherein said equipment control action is with respect to said laser.

34. The method of claim 32, further comprising the step of receiving equipment data representing conditions of said deposition and wherein said equipment control action is further based on said equipment data.

35. The method of claim 30, wherein said subject film is a superconducting film and said known chemical characteristics are related to critical temperature.

36. The method of claim 30, wherein said step of acquiring film response data is performed by irradiating said subject film via optical fiber and acquiring a Raman response.

37. The method of claim 30, wherein said step of acquiring film response data is performed by irradiating said subject film and acquiring the Raman response via optical fiber.

38. The method of claim 30, wherein said step of acquiring film response data is performed by irradiating said subject film with near infra red light and acquiring a Raman response.

39. The method of claim 30, further comprising the step of identifying at least one known chemical characteristic of said subject film on the basis of said comparing step.

* * * * *